(12) United States Patent
Gao

(10) Patent No.: US 9,452,214 B2
(45) Date of Patent: Sep. 27, 2016

(54) GARMENT FABRIC

(71) Applicant: Jie Gao, Sutton Coldfield (GB)

(72) Inventor: Jie Gao, Sutton Coldfield (GB)

( * ) Notice: Subject to any disclaimer, the term of this patent is extended or adjusted under 35 U.S.C. 154(b) by 146 days.

(21) Appl. No.: 14/227,592

(22) Filed: Mar. 27, 2014

(65) Prior Publication Data

US 2015/0272901 A1 Oct. 1, 2015

(51) Int. Cl.
| | | |
|---|---|---|
| A61K 36/00 | (2006.01) | |
| A61K 45/06 | (2006.01) | |
| B32B 7/12 | (2006.01) | |
| B32B 5/02 | (2006.01) | |
| B32B 5/26 | (2006.01) | |
| A41B 11/00 | (2006.01) | |
| A61K 9/70 | (2006.01) | |

(52) U.S. Cl.
CPC ............ *A61K 45/06* (2013.01); *B32B 5/024* (2013.01); *B32B 5/26* (2013.01); *B32B 7/12* (2013.01); *A41B 11/00* (2013.01); *A41D 2400/34* (2013.01); *A61K 9/7053* (2013.01); *A61K 36/00* (2013.01); *B32B 2260/021* (2013.01); *B32B 2260/048* (2013.01); *B32B 2264/105* (2013.01); *B32B 2307/208* (2013.01); *B32B 2307/7145* (2013.01); *B32B 2437/00* (2013.01)

(58) Field of Classification Search
None
See application file for complete search history.

(56) References Cited

FOREIGN PATENT DOCUMENTS

| | | | |
|---|---|---|---|
| CN | 101961149 A | * | 2/2011 |
| JP | 2003 94809 A | | 10/1991 |
| JP | 2003 88412 A | | 3/2003 |
| JP | 2012 525123 A | | 10/2012 |
| JP | 12525123 A | | 10/2012 |
| KR | 100419478 B1 | * | 2/2004 |

OTHER PUBLICATIONS

Hikari Nai-Gai Patent Office—Reasons for Rejection Oct. 16, 2015.

* cited by examiner

*Primary Examiner* — Qiuwen Mi
(74) *Attorney, Agent, or Firm* — Clifford H. Kraft

(57) ABSTRACT

A garment fabric comprises a fabric support (11) for defining the shape of a garment and having a surface to at least a part of which there is secured a therapeutic fabric layer (14) by means of a flexible adhesive which comprises a herb ingredient, said flexible adhesive at least partially penetrating into each of the fabric support and the therapeutic fabric layer to provide chemical adhesion and a mechanical interlock between said layers. For forming the garment fabric the fabric support and the therapeutic fabric layer each have a layer (15, 16) of adhesive applied thereto prior to bringing the two layers of fabric into contact with one another, with the adhesive material sandwiched therebetween.

6 Claims, 1 Drawing Sheet

GARMENT FABRIC

BACKGROUND

1. Field of the Invention

This invention relates to a garment fabric which provides a beneficial effect when worn over an area of skin which, for one or more reasons, has suffered damage.

2. Description of the Prior Art

Frequently skin damage can arise in consequence of climatic factors, especially in low temperature and low humidity situations, and in consequence of environmental factors such as may be caused by contact with substances such as lime, cement and salt. Also, skin damage can be associated with genetic factors, bacterial disease and, especially in the case of older people, physiological factors.

Many women have damaged heel skin, which can be embarrassing when wearing slippers of other, summer type footwear such as flip-flops. Also there is discomfort in winter when large cracks can arise and result in bleeding.

It is already known to form a garment such as a sock from fibres or filaments which have antibacterial properties, for example by providing a fibrous material which contains nano-silver particles of a diameter less than 100 nm as described in EP 1490543A.

These antibacterial properties assist in providing a relatively healthy environment for an area of skin which has suffered damage due to bacterial disease and thus provide a relatively healthy environment which assists the natural processes of skin recovery. However, alone the anti-bacterial properties are of limited effectiveness for ensuring or assisting a speedy recovery.

The speed of recovery from skin damage often can be improved by ensuring a good rate of blood circulation. It is known that repair of damaged skin can be assisted by use of a cream, but often individuals forget to apply the cream regularly. It is known also to employ medication such as zinc oxide, snake oil, Vaseline (RTM) and sulphur ointment, but such treatments are inconvenient and generally expensive.

It would be advantageous if the rate of recovery and or ease of recovery could be accelerated and the present invention seeks to provide a garment fabric which addresses this matter.

SUMMARY OF THE INVENTION

According to one aspect of the present invention there is provided a garment fabric comprising a fabric support in the form of a layer for defining the shape of a garment and having a surface to at least a part of which there is secured a therapeutic fabric layer, said therapeutic fabric layer being secured to the fabric support by a flexible adhesive which comprises a herb ingredient, said flexible adhesive at least partially penetrating into each of the fabric support and the therapeutic fabric layer to provide chemical adhesion and a mechanical interlock between said layers.

DESCRIPTION OF THE PREFERRED EMBODIMENT

Figure 1:
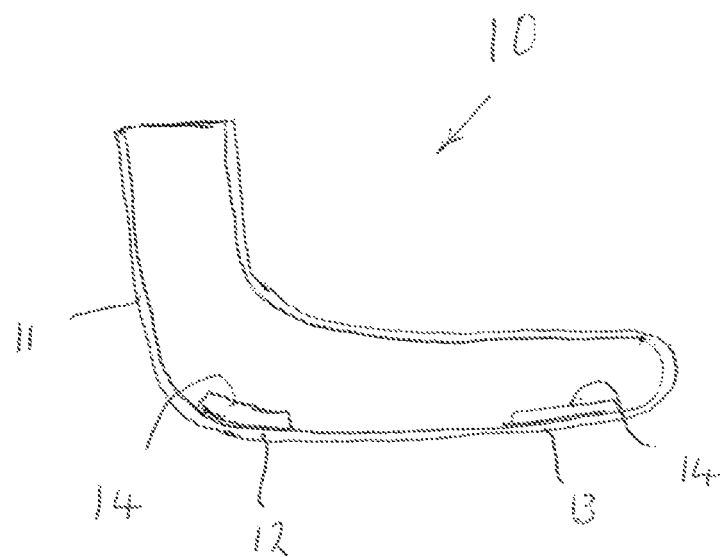
FIG. 1 is a sectional view of a sock in accordance with an embodiment of the present invention.

Preferably said therapeutic fabric layer comprises fibres or filaments, such as woven nylon or other filaments, which have antibacterial properties and comprise magnetic particles.

The terms "fibres" and "filaments" are used herein to refer respectively to filamentary elements of a relatively short length, and to filamentary elements of a relatively long length, and to embrace yarns, cords and other such assemblies comprising a plurality of fibres and/or filaments.

Preferably the herb ingredient is a Chinese herb ingredient and preferably the flexible adhesive comprises one or more of fang fend, jing jie, tou gu cao, dang gui, hong hua, ding Xiang, chuan jiao, ai ye and jiang zhen Xiang.

For providing pain relief the flexible adhesive preferably comprises ding Xiang. For open sweat pores it preferably comprises one or more of fang feng, jing jie and tou gu can, and more preferably it comprises the combination of all three of said herb ingredients. For a deoppilant benefit preferably it comprises ai ye. For promotion of blood circulation preferably it comprises zhen Xiang and/or hong hua.

Said fabric support may be of a type having anti-bacterial properties.

Said therapeutic layer additionally may comprise one or more of sulphur, zinc oxide, allantoin and lanolin.

The term "fabric" is used herein to refer to a material which has been formed from fibres and or filaments which have been brought together by a process such as weaving, knitting or felting to result in a cohesive assembly of the filaments and or fibres.

The adhesive may be of a type prepared by filtering of natural latex to remove any impurities, followed by mixing with a said herb ingredient and optionally, with one or more of potassium hydroxide (KOH), allantoin, accelerating agent (such as PX) and acetylsalicylic acid.

The flexible adhesive layer preferably comprises two adhesive layers. One layer may comprise natural rubber mixed with a said herb ingredient and the other may comprise natural rubber that has been mixed with one or more of potassium hydroxide, allantoin and acetylsalicylic acid.

The therapeutic fabric layer may be of a type comprising fibres or filaments which have been rendered anti-bacterial by a technique known per se, such as that described in the aforementioned EP 1490543. Optionally the fabric support also may possess anti-bacterial properties.

The therapeutic fabric layer preferably has a thickness less than 1.0 mm (0.04 inches), preferably less than 0.5 mm (0.02 inches). A thickness of 0.2 mm (0.01 inches) or less is preferred for many applications.

Preferably the therapeutic fabric layer is provided with anti-bacterial properties by treatment of the fibres or filaments with a colourless, transparent type of nano-silver solution which may be of an acidic, neutral or alkaline type. The nano-silver solution preferably comprises silver particles which have a size less than or equal to 0.5 nm.

The fibres or filaments of the therapeutic fabric layer may be fibres or filaments of a natural material such as cotton or wool or of a synthetic material such as a polyamide, for example nylon or an aromatic polyamide.

The flexible adhesive layer may incorporate other materials such as sulphur, zinc oxide and lanolin to further enhance medical benefits.

Preferably use is made of a therapeutic fabric layer having an average magnetic flux of greater than 0.35 mm mwb.

The therapeutic fabric layer preferably is effective to reflect body heat, particularly to reflect infrared rays having a wavelength of 8-14 μm.

The therapeutic fabric layer may be provided as a lining within all or part of a sock or other garment such as a glove. It may be in the form of a pad which is adhered to a part of that surface of a garment which confronts the skin of the wearer. White cotton is a particularly suitable material for forming pads.

The fabric support may be made of material such as cotton, nylon, a mix of cotton and nylon, a mix of wool and cotton, bamboo fabric, linum fibre, infra-red fabric and magnetic fabric. Other known materials may be employed to form the fabric support and define the shape of a garment.

In accordance with another aspect of the present invention there is provided a method for the production of a garment fabric which comprises a support layer to at least a part of which there is secured a therapeutic layer, said method comprising providing a first adhesive which comprises a herb ingredient and applying said first adhesive to one of the support layer and therapeutic layer, providing a second adhesive comprising natural rubber mixed with one or more of potassium hydroxide, allantoin and acetylsalicylic acid, applying said second adhesive to the other of said therapeutic layer and support fabric and then bringing together of the two adhesive layers into contact with one another thereby to secure the therapeutic layer to at least a part of the surface of the support layer.

Preferably the first adhesive comprises a mixture of natural rubber and a herb ingredient such as one or more of the Chinese herbs fang fend, jing jie, tou gu cao, dang gui, hong hua, ding Xiang, chuan jiao, ai ye and jiang zhen Xiang. Preferably the herb ingredients are incorporated by mixing slowly with natural rubber at a temperature no less than 15° C. Preferably the first adhesive is applied to the therapeutic layer but may alternatively be applied to the support layer. Preferably it is applied to a thickness of 0.01 mm (0.005 inches).

The second layer of the adhesive preferably is applied to the fabric support but may alternatively be applied to the therapeutic fabric layer. Preferably the second adhesive is applied to a thickness of 0.01 mm (0.005 inches). Other thicknesses may be employed and preferably the thicknesses of each of the two adhesive layers of the flexible adhesive layer are substantially equal.

Preferably the two layers are initially held in contact with one another at a temperature of no less than 20° centigrade. It is further preferred that the method comprise a delay of at least two minutes, preferably at least five minutes between coating adhesive to the layers and bringing them into contact with one another.

An embodiment of the present invention will now be described, by way of example only, with reference to the accompanying diagrammatic drawing (FIG. 1) which is a sectional view of a sock in accordance with the present invention and the sectional view (FIG. 2) of part of the sock to show the adhesive layers.

Figure 2:
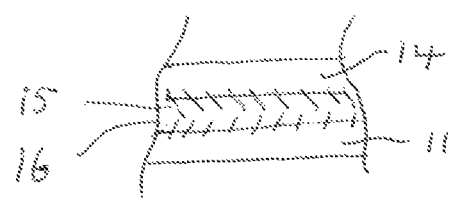
FIG. 2 shows part of the sock with adhesive layers.

A sock 10, see FIG. 1, comprises a stretchable outer fabric layer 11 which is of a flexible anti-bacterial material and defines the shape of the sock. The sock comprises a heel region 12 and a sole region 13 which, in use, aligns with the ball of the wearer's foot. Each of the regions 12, 13 is provided with a flexible therapeutic fabric pad 14 of a type in accordance with the present invention. In this embodiment the pads each have a thickness of 0.2mm (0.01 inches) and comprise woven nylon filaments. The nylon filaments are of a type which have adopted sub-nanometer zirconium phosphate carrying silver particles. The filaments are also of a type which exhibit far infrared and anti-bacterial properties.

The pads are held in position by a flexible adhesive layer comprising natural latex and which partially penetrates into the fabric material of the layer 11 and the pads 14. In addition to chemical adhesion the interposed natural latex effects a mechanical interlock with the filaments of the layer 11 and of the pads 14.

In this embodiment of the present invention the flexible adhesive layer comprises a first adhesive 15 which is a mixture of natural latex and one or more of the Chinese herb ingredients fang fend, jing jie, tou gu cao, dang gui, hong hua, ding Xiang, chuan jiao, ai ye and jiang zhen Xiang. The first adhesive layer is formed by slowly mixing the herb ingredient(s) with natural latex at a temperature no less than 15° C.

A second adhesive 16 is formed by mixing natural latex with potassium hydroxide, allantoin and acetylsalicylic acid.

The first adhesive 15 is applied as a layer to the pads 14 and the second adhesive 16 is applied as a layer to those parts of the fabric layer 11 which are to receive the pads 14. The two adhesives are applied to form layers having a thickness of 0.005 inches. The two adhesive layers are held apart for two minutes and then brought together at a temperature of no less than 20° C.

A sock or other garment in accordance with the present invention is believed to provide an improved ability to speed the recovery of damaged skin in consequence of the anti-bacterial properties that have been found advantageously to enhance the rate of blood microcirculation and viscosity. Thus the need to employ relatively inconvenient treatments such as ointments may be avoided.

In particular, in the case of damaged heels or other parts of feet the use of socks of a type in accordance with the present invention is more convenient than, for example, the use of ointments and because the use of socks is a very normal practice the need for routine and regular treatment is less likely to be forgotten than is the use of ointments.

Several descriptions and illustrations have been presented to aid in understanding the present invention. One with skill in the art will realise that numerous changes and variations are possible without departing from the spirit of the invention. Each of these changes and variations is within the scope of the present invention.

The invention claimed is:

1. A garment fabric comprising a fabric support in the form of a layer for defining the shape of a garment and having a surface to at least a part of which there is secured a therapeutic fabric layer, said therapeutic fabric layer being secured to the fabric support by a flexible adhesive, said flexible adhesive at least partially penetrating into each of the fabric support and the therapeutic fabric layer to provide both chemical adhesion and a mechanical interlock between said layers, and said flexible adhesive comprising a first layer of adhesive and a second layer of adhesive wherein the first layer of adhesive comprises a layer of natural rubber containing one or more of the herb ingredients fang feng, jing jie, tou gu cao, dang qui, hong hua, ding Xiang, chuan jiao, ai ye and jiang zhen Xiang, and wherein the second layer of adhesive comprises natural rubber mixed with one or more of potassium hydroxide, allantoin and acetylsalicylic acid.

2. A garment fabric according to claim 1 wherein the therapeutic fabric layer comprises woven filaments.

3. A garment fabric according to claim 1 wherein the therapeutic fabric layer comprises a material having anti-bacterial properties.

4. A garment fabric according to claim 1 wherein the therapeutic fabric layer comprises fibers or filaments which comprise magnetic particles.

5. A garment fabric according to claim 1 wherein the therapeutic fabric layer has a thickness less than 0.04 inches (1.0 mm).

6. A sock comprising a fabric support which defines the shape of the sock, and having a surface to at least a part of which there is secured a therapeutic fabric layer of a thickness less than 0.04 inches, said therapeutic fabric layer being secured to the fabric support by a flexible adhesive, said therapeutic fabric layer having antibacterial properties and comprising woven filaments which comprise magnetic particles, said flexible adhesive at least partially penetrating into each of the fabric support and the therapeutic fabric layer to provide chemical adhesion and a mechanical interlock between said layers, and said flexible adhesive comprising a first layer of adhesive and a second layer of adhesive wherein the first layer of adhesive comprises a layer of natural rubber containing one or more of the herb ingredients fang feng, jing jie, tou gu cao, dang qui, hong hua, ding Xiang, chuan jiao, ai ye and jiang zhen Xiang, and wherein the second layer of adhesive comprises natural rubber mixed with one or more of potassium hydroxide, allantoin and acetylsalicylic acid.

\* \* \* \* \*